United States Patent [19]

Jones

[11] Patent Number: 5,055,671

[45] Date of Patent: Oct. 8, 1991

[54] APPARATUS FOR DETECTING TRANSDUCER MOVEMENT USING A FIRST AND SECOND LIGHT DETECTOR

[75] Inventor: Paul H. Jones, Mercer Island, Wash.

[73] Assignee: SpaceLabs, Inc., Redmond, Wash.

[21] Appl. No.: 592,230

[22] Filed: Oct. 3, 1990

[51] Int. Cl.⁵ .............................................. H01J 5/16
[52] U.S. Cl. ............................. 250/227.21; 128/667; 356/41
[58] Field of Search ...................... 250/227.11, 227.21; 128/664–667; 356/39, 40, 41, 42

[56] References Cited

U.S. PATENT DOCUMENTS

| | | | |
|---|---|---|---|
| 3,095,872 | 7/1963 | Tolles | 128/672 |
| 3,825,342 | 7/1974 | Lubbers et al. | 356/41 |
| 3,970,394 | 7/1976 | Stanton | 250/227.11 |
| 4,476,875 | 10/1984 | Nilsson et al. | 128/666 |
| 4,494,550 | 1/1985 | Blazek et al. | 128/666 |
| 4,590,948 | 5/1986 | Nilsson | 128/666 |
| 4,854,699 | 8/1986 | Edgar, Jr. | 356/41 |

Primary Examiner—David C. Nelms
Assistant Examiner—S. Allen
Attorney, Agent, or Firm—Seed and Berry

[57] ABSTRACT

An apparatus for photo-optically detecting transducer motion in a transducer using a photodetector elastically suspended inside the transducer housing and photo-optically coupled to a light source. During movement the inertia effect of the photodetector along with the elastic suspension system causes the changes in the photo-optical coupling between the photodetector and the light source. The inertia effect of the photodetector is enhanced by adding a mass to the photodetector. Either the magnitude or the phase of the photodetector output is monitored to detect movement.

16 Claims, 5 Drawing Sheets

APPARATUS FOR DETECTING TRANSDUCER MOVEMENT USING A FIRST AND SECOND LIGHT DETECTOR

DESCRIPTION

1. Field of the Invention

The instant invention relates to movement detection. More particularly, it relates to an apparatus which detects transducer movement during photo-optical scanning.

2. Description of the Prior Art

Photoplethysmographs are well known instruments for determining and registering variations in the blood volume present or passing through tissue using light sources. A specific application of photoplethysmography is non-invasive pulse oximetry, the measurement of arterial hemoglobin oxygen saturation.

Pulse oximeters have a transducer that is applied to a patient during measurement. This transducer has at least one light source, generally a light-emitting diode (LED), which transmits light through the patient's skin and into his subcutaneous tissues. A portion of the light is received by a photodetector and is converted into an electrical output called a working signal. The working signal may result from reflections of the light from the patient's tissue and blood, the reflective mode of operation, or it may result from light which has passed completely through the patient's tissue, the transillumination mode of operation. Ideally, the working signal varies only in response to changes in blood volume. However, transducer movements may affect the working signal by causing it to vary in response to transducer movement. This dependency on transducer movement, called motion artifact, is undesirable and can obscure the variations caused by blood volume changes.

Motion artifact is well known, and pulse oximeter manufacturers have taken steps to reduce its effects. However, these steps are generally ineffective unless the transducer movement is first detected, something that is particularly difficult to do when the motion artifact occurs in conjunction with the patient's pulse.

It is clear that there has existed a need for a simple, low cost apparatus for detecting transducer movement.

SUMMARY OF THE INVENTION

It is an object of the present invention to provide an apparatus and method for detecting transducer movement.

To achieve the foregoing object and others, the present invention detects transducer movement by (1) amplifying changes in the photo-optical coupling between a photodetector and a light source, and (2) detecting the transducer movement by monitoring the changes in the photo-optical coupling. In a better embodiment, three photodetectors are elastically mounted so that transducer movement changes the photo-optical coupling between the light source and each photodetector differently. Preferably, the three photodetectors are mounted symmetrically on a circular, plate with different masses attached to each photodetector.

DETAILED DESCRIPTION OF THE PREFERRED EMBODIMENT

Figure 1:
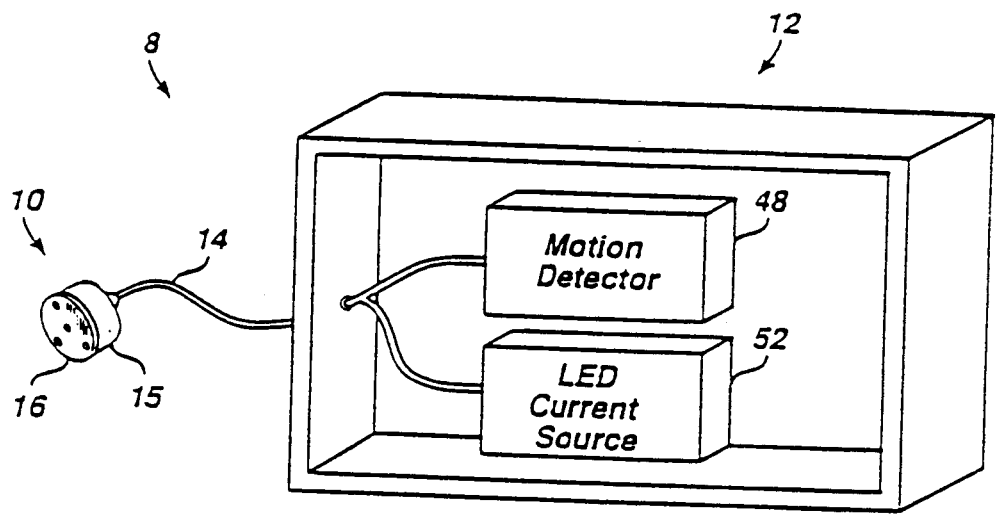
FIG. 1 is a simplified isometric view of a pulse oximeter according to the preferred embodiment of the present invention.

With reference to FIG. 1, a pulse oximeter 8 according to the preferred embodiment includes a transducer 10, a pulse oximeter chassis 12, and a cable 14. The operation and description of these assemblies is described below.

Figure 2:
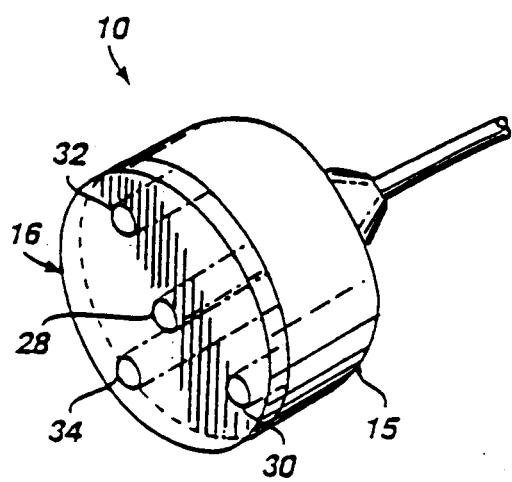
FIG. 2 is an isometric view of a pulse oximeter transducer according to the preferred embodiment.

Referring now to FIG. 2, the transducer 10 has a housing 15 with a circular plate 16 as a bottom surface. The plate 16 contacts a patient during pulse oximetry. The transducer housing 15 is preferably rigid, except for the plate 16, to support and protect the components within the transducer 10. In operation, the transducer 10 is maintained in a relatively fixed position on a patient by use of adhesive tape (not shown).

Figure 3:
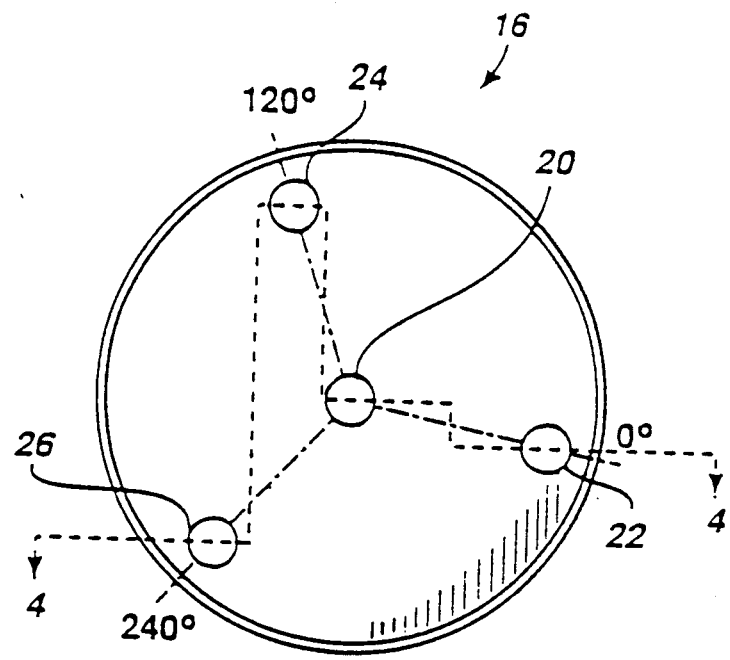
FIG. 3 is a bottom view of a plate used in the transducer of FIG. 2.

The plate 16, best illustrated in FIG. 3, is ideally made from a resilient, flexible material that supports holes without tearing and has good adhesive properties with an adhesive compound 18 used to mount components. However, a rigid plate 16 would also work, albeit with reduced results. While the preferred material for plate 16 is silicon rubber, other materials are suitable and will be well known to those in the art. Likewise, numerous materials are suitable for the construction of the transducer housing 15.

Referring again to FIG. 3, a centrally located LED opening 20 is disposed through the plate 16. Additionally, the plate 16 has symmetrical concentric openings: 0° opening 22, 120° opening 24, and 240° opening 26, disposed through it. These openings are preferably located about two-thirds of the way between the center and the outer periphery of the plate 16. They are named for their angular positions relative to the 0° opening 22, which, because of symmetry, is selectable at random. All openings are easily formed using conventional methods such as a hole punch.

Figure 4:
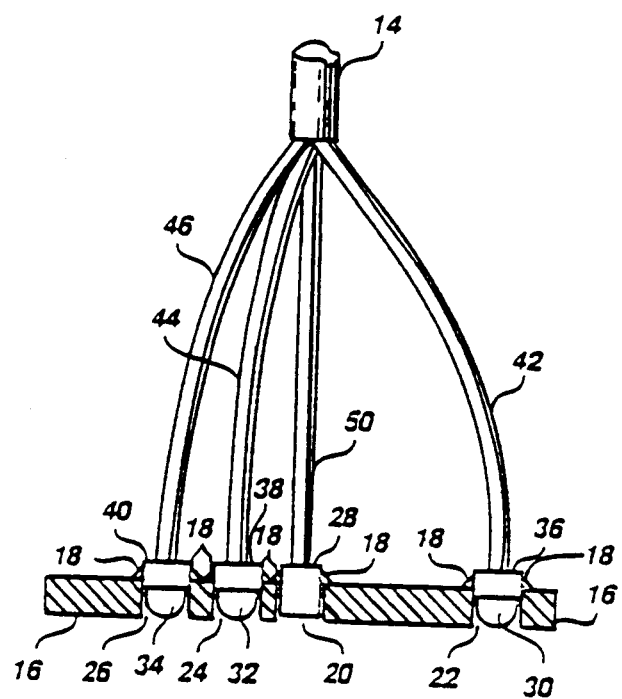
FIG. 4 is side-on, cut-away view showing the plate of FIG. 3 and the components which mount thereto.

Referring now to FIG. 4, a cut-away view of FIG. 3 taken along FIG. 3's dashed lines, a light-emitting diode 28 is attached to the plate 16 in the LED opening 20. Similarly, a 0° photodetector 30, a 120° photodetector 32, and a 240° photodetector 34 are attached to the plate 16 in the 0° opening 22, the 120° opening 24, and the 240° opening 26, respectively. Attachment of these components to the plate 16 is performed by the adhesive compound 18, previously mentioned.

The photodetectors 30, 32, and 34, are preferably silicon photodiodes, but other photodetectors, such as photodiodes made from other semiconductor compounds, phototransistors, or photoresistors, are also suitable. Similarly, while the light source, (light-emitting diode 28 in the preferred embodiment) is preferably a light-emitting diode, other light sources such as a laser or an incandescent bulb could also be used. Whatever embodiments are chosen, the photodetectors must create sufficient working signals from light from the light source for system operation.

Referring again to FIG. 4, a 0° mass 36, a 120° mass 38, and a 240° mass 40 are rigidly attached to the 0° photodetector 30, the 120° photodetector 32 and the 240° photodetector 34, respectively. Each mass is unique in magnitude and is attached to its photodetector by the adhesive compound 18.

Figure 5:
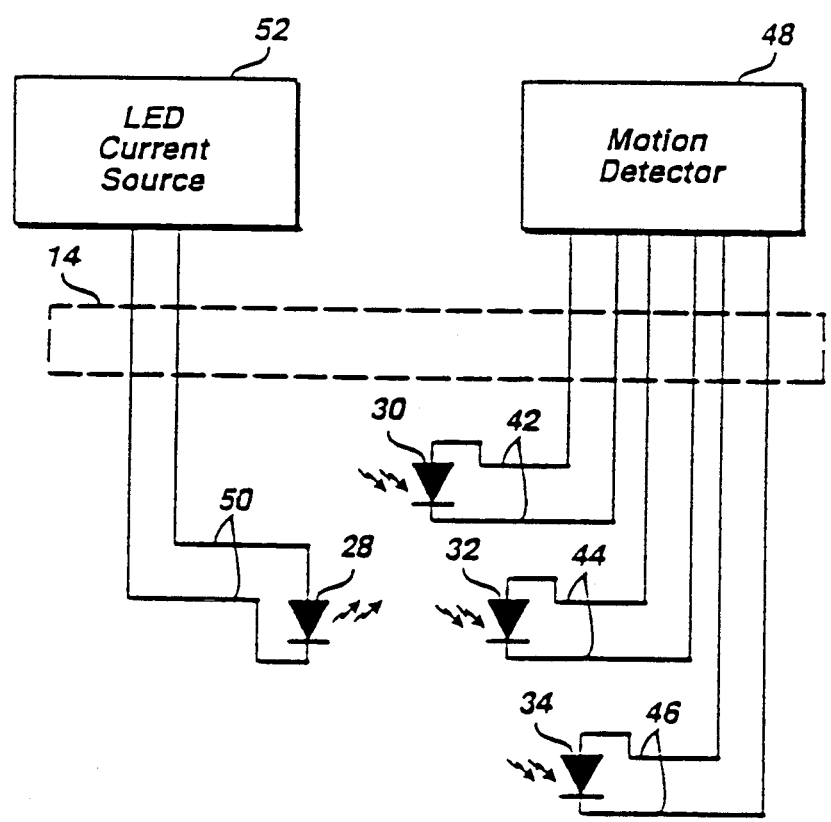
FIG. 5 is a partial schematic diagram, partial block diagram of the pulse oximeter shown in FIG. 6.

Referring now to FIGS. 1, 4, and 5 as required, the 0° photodetector 30, the 120° photodetector 32, and the 240° photodetector 34 have leads 42, 44, and 46, respectively, which, via the cable 14, electrically connect to a motion detector network 48. Also, cable 14 connects the light-emitting diode 28 having leads 50 to an LED current source 52. The motion detector network 48 and the LED current source 52 are both within the pulse oximeter chassis 12.

Referring now to FIG. 5, the LED current source 52 injects current into the light-emitting diode 28, causing it to emit light. Some of the light from the light-emitting diode 28 reflects from the patient's subcutaneous tissues and returns to the 0° photodetector 30, the 120° photodetector 32, and the 240° photodetector 34, creating working signals. These working signals are applied to the motion detection network 48 which is able to detect changes to the proportionality and/or phase relationships of the working signals.

Figure 6:
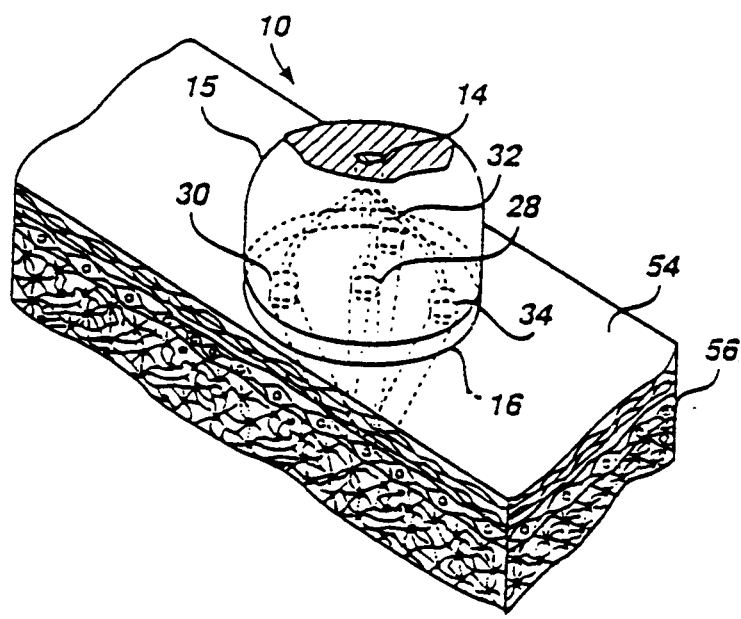
FIG. 6 is an operational diagram of the transducer of FIG. 2 attached to a patient.

System operation can be understood by referring to FIGS. 4, 5, and 6 as required while reading the following discussion. With the transducer 10 contacting the patient's skin 54, the LED current source 28 causes the light emitting diode 28 to emit light which penetrates the patient's skin. Some of this light reflects from the patient's subcutaneous tissue 56 onto the photodetectors 30, 32, and 34, creating working signals. While these working signals are not, in general, the same, they are substantially stable and maintain their relative relationships as long as the photo-optical couplings between the light-emitting diode 28 and the photodetectors 30, 32, and 34 remains constant.

Movement of the transducer 10 changes the light paths and the photo-optical couplings between the light emitting diode 28 and the photodetectors 30, 32, and 34. The photo-optical coupling changes are enhanced by the resilient suspension system formed by the plate 16, the photodetectors 30, 32, and 36, and the masses 36, 38, and 40. Inertia effects during transducer acceleration causes each photodetector/mass combination to move the plate 16 differently. This causes each working signal to change differently. The working signal differences are then detected by the motion detector 48. Once transducer movement is detected, various methods such as corrective mathematical algorithms or simply disabling measurement during movement may be used to reduce the effects of motion artifact.

While preferably three photodetectors are used, it is possible to detect transducer movement with only one photodetector. Assuming, for convenience, that a photodetector is mounted with a mass on a flexible plate, transducer acceleration would cause the plate to flex, causing changes in the photo-optical coupling. However, detecting these changes is difficult since the working signal can only use itself as a reference.

Using two photodetectors substantially improves movement detection since changes can be detected by comparing working signals to each other. However, transducer movement can occur such that the relationships between the working signals do not change, despite changes in the photo-optical couplings. To understand this, consider movement in a direction perpendicular to a line between the two photodetectors. Ideally, any changes in the two working signals would be common to both and thus detecting changes by comparing the two working signals would not detect movement. While actual working signal changes are more complicated than that suggested, it is nevertheless not believed possible to guarantee detection of all movements with only two photodetectors.

However, adding a third photodetector allows for simple detection of movement in any direction, except possibly the Z-axis (perpendicular to the plane containing all three photodetector). A comparison of the amplitudes or phases of the working signal at any photodetector with those of the other two photodetectors will detect motion. The problem with Z-axis movement detection is that if all suspension system are the same, then Z-axis movement will causes the same photo-optical coupling changes. This problem is overcome by making each photodetector suspension system different. In the preferred embodiment, each photodetector suspension system is made different by adding different masses to each photodetector.

Figure 7:
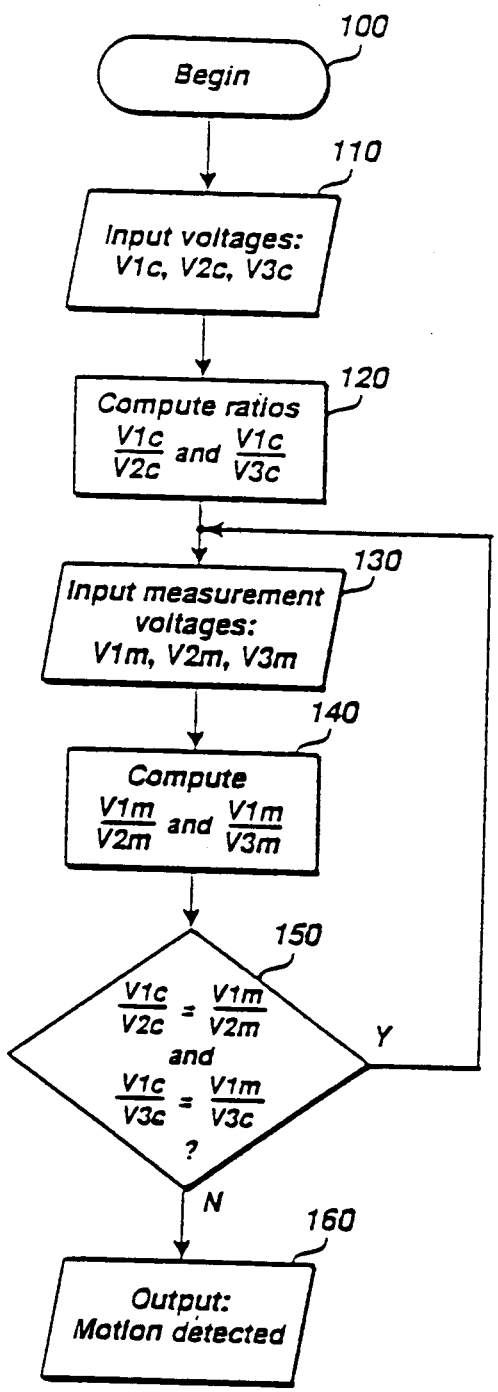
FIG. 7 is a functional flow diagram depicting one method of sensing transducer motion from changes in the working signals.

A method of detecting changes in the proportionality and/or phase relationships of the working signals is illustrated by the flow diagram of FIG. 7. This method will work equally well with changes in the working signals' phase relationships or voltages. For convenience, FIG. 7 will be discussed in terms of changes in working signal voltages. In block 100, motion detection begins. At a calibration time, the voltage outputs from the motion detector 48, resulting from working signals from the 0° photodetector 30, the 120° photodetector 32, and the 240° photodetector 34 are input as voltages $V1c$, $V2c$, and $V3c$, respectively, as indicated in block 110. These voltages are used, as shown in block 120, to compute two ratios, $V1c + V2c$, and $V1c + V3c$. These ratios are stored for later use. Subsequent voltages from the motion detector 48, corresponding to the working signals from the 0° photodetector 30, the 120° photodetector 32, and the 240° photodetector 34 are input as measurement voltages $V1m$, $V2m$, and $V3m$, respectively, as indicated in block 130. These voltages are used to compute, as shown in block 140, two additional ratios, $V1m + V2m$, and $V1m + V3m$. As shown in block 150, motion is sensed by comparing the ratio $(V1c + V2c)$ to the ratio $(V1m + V2m)$, and the ratio $(V1c + V3c)$ with the ratio $(V1m + V3m)$. If the equated ratios are the same, the transducer 10 has not moved. However, if one or both of the equated ratios are unequal, then it is known that the transducer 10 has moved. If the ratios have not changed, the new input measurement is taken and new ratios are computed, and the operation of block 150 is repeated. However, if motion has occurred, then as shown in block 160, a signal is output showing that transducer motion has occurred. The calibration voltages $V1c$, $V2c$, and $V3c$ can be updated at fixed times, or they can be updated continuously with the last values of $V1m$, $V2m$, and $V3m$, respectively.

It should be understood that the flex plate/photodetector/mass arrangement of the preferred embodiment is not unique and other arrangements can achieve the same results. For example, the masses could be mounted directly on the plate near the photodetectors, or the photodetectors could be mounted on a spring suspension system instead of a plate.

Since the preferred embodiment is a reflective mode pulse oximeter, the light source (light-emitting diode 28) is conveniently mounted on the plate. However, transillumination mode pulse oximeters can also use the present invention. In their case, the light source would be separate from the transducer housing and the light path would be through the patient's tissue.

The above described apparatus has been presented for the purpose of illustrating, but not limiting, the invention. Various modifications will come readily to the mind of one skilled in the art, and will be within the scope of the invention a defined in the appended claims.

I claim:

1. A motion-sensing transducer, comprising:
   a light emitter;
   a first light detector optically coupled to said light emitter;
   means for resiliently mounting said first light detector in said transducer so that said first light detector is displaced by acceleration imparted to said transducer thereby modulating the light optically coupled from said light emitter to said first light detector;
   a second light detector optically coupled to said light emitter; and
   means for comparing the light coupled from said light emitter to said first light detector with the light coupled from said light emitter to said second light detector whereby movement of said transducer is detected by variations in the light coupled to said first light detector relative to the light coupled to said second light detector.

2. The motion-sensing transducer of claim 1 further including means for resiliently mounting said second light detector in said transducer so that said second light detector is displaced by acceleration imparted to said transducer thereby modulating the light optically coupled from said light emitter to said second light detector.

3. The motion-sensing transducer of claim 2 wherein respective masses are physically coupled to said first and second light detectors to amplify the acceleration induced displacement of said light detectors.

4. The motion-sensing transducer of claim 3 wherein said masses are attached directly to their respective light detectors.

5. The motion-sensing transducer of claim 2 wherein said means for resiliently mounting said first light detector in said transducer provides said first light detector with suspension characteristics different from the suspension characteristics provided to said second light detector by said means for resiliently mounting said second light detector in said transducer thereby increasing the differences between the acceleration induced movement of said first light detector and the acceleration induced movement of said second light detector.

6. The motion-sensing transducer of claim 5 wherein different masses are physically coupled to said first and second light detectors to provide said first and second light detectors with different suspension characteristics.

7. The motion-sensing transducer of claim 1, further comprising:
   a third light detector optically coupled to said light emitter;
   means for resiliently mounting said third light detector in said transducer so that said third light detector is displaced by acceleration imparted to said transducer thereby modulating the light optically coupled from said light emitter to said third light detector; and
   means for comparing the light coupled from said light emitter to said third light detector with the light coupled from said light emitter to either said first or said second light detector whereby movement of said transducer is detected by variations in the light coupled to said third light detector relative to the light coupled to said first or said second light detector.

8. The motion-sensing transducer of claim 7 wherein said first, second and third light detectors are positioned symmetrically around said light emitter.

9. The motion-sensing transducer of claim 1 wherein said means for resiliently mounting said first light detector in said transducer includes a resilient plate on which said first light detector is mounted.

10. The motion-sensing transducer of claim 1 wherein the optical coupling from said light emitter to said first light detector is further modulated by a medical parameter being sensed so that said first light detector is used to sense said medical parameter and to sense movement of said transducer.

11. A method of sensing movement of a transducer having a light emitter and first and second light detectors optically coupled to said light emitter and generating respective working signals indicative of the light coupled to said first and second light detectors, said method comprising:
   resiliently mounting at least one of said light detectors in said transducer so that said resiliently mounted light detector is displaced by acceleration imparted to said transducer thereby modulating the light optically coupled from said light emitter to said resiliently mounted light detector; and
   comparing said working signals to each other so that movement of said transducer is indicated by variations in the differences between said first and second working signals.

12. The method of claim 11, further including the step of resiliently mounting both of said light detectors in said transducer so that both of said light detector are displaced by acceleration imparted to said transducer.

13. The method of claim 12, further including the step of physically coupling respective masses to said light detectors to amplify the acceleration induced displacement of said light detectors.

14. The method of claim 12, further including the step of making the suspension characteristics of each of said light detectors different from each other so that said light detectors are displaced differently from each other responsive to acceleration imparted to said transducer.

15. The method of claim 14 wherein said step of making the suspension characteristics of each of said light detectors different from each other is accomplished by physically coupling different masses to said light detectors.

16. The method of claim 11 wherein the optical coupling from said light emitter to said first light detector is further modulated by a medical parameter being sensed, and wherein said method further includes using said working signals to sense said medical parameter and to sense movement of said transducer.

* * * * *